United States Patent
Sangha

(10) Patent No.: US 8,241,593 B2
(45) Date of Patent: Aug. 14, 2012

(54) SPECIMEN TRAY

(75) Inventor: Jangbir S. Sangha, Overland Park, KS (US)

(73) Assignee: The Bode Technology Group, Inc., Lorton, VA (US)

( * ) Notice: Subject to any disclaimer, the term of this patent is extended or adjusted under 35 U.S.C. 154(b) by 1060 days.

(21) Appl. No.: 11/703,494

(22) Filed: Feb. 7, 2007

(65) Prior Publication Data
US 2007/0258857 A1    Nov. 8, 2007

Related U.S. Application Data

(60) Provisional application No. 60/797,534, filed on May 4, 2006, provisional application No. 60/813,476, filed on Jun. 14, 2006.

(51) Int. Cl.
*B01L 9/00* (2006.01)

(52) U.S. Cl. ............ 422/560; 422/63; 422/65; 422/563; 422/566

(58) Field of Classification Search .................... 422/63, 422/65, 99, 101, 102, 104, 560, 563, 566
See application file for complete search history.

(56) References Cited

U.S. PATENT DOCUMENTS

| 6,874,634 B2 * | 4/2005 | Riley ........................ 206/439 |
| 2002/0039796 A1 * | 4/2002 | Dores et al. .................. 436/177 |
| 2006/0153736 A1 * | 7/2006 | Kalra et al. .................... 422/57 |

* cited by examiner

*Primary Examiner* — Jill Warden
*Assistant Examiner* — Dwayne K Handy
(74) *Attorney, Agent, or Firm* — Polsinelli Shughart PC; Richard P. Stitt

(57) ABSTRACT

A holder for a plurality of biological specimen collection devices having collection absorbents extending therefrom is provided, the holder operating to organize and identify the collection devices and operating to position the collection devices for extraction of sample portions from each of the collection absorbents of the multiple collection devices while positioning a sample punch absorbent cleaning strip adjacent the collection absorbent of each device to allow cleaning of the sample punch between each use.

7 Claims, 7 Drawing Sheets

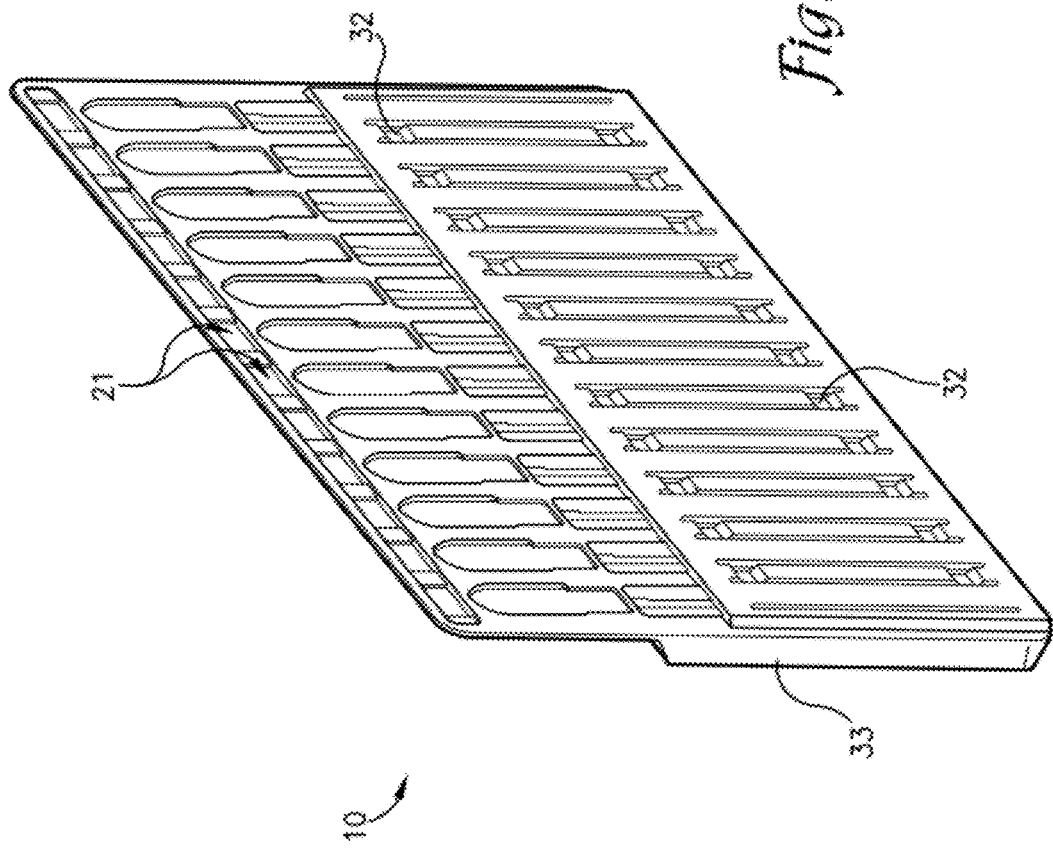

SPECIMEN TRAY

CROSS-REFERENCE TO RELATED APPLICATION

This application claims priority under 35 U.S.C. 119(e) and 37 C.F.R. 1.78(a)(4) based upon copending U.S. Provisional Application Ser. No. 60/797,534 for SPECIMEN TRAY, filed May 4, 2006 and U.S. Provisional Application Ser. No. 60/813,476 for SPECIMEN TRAY, filed Jun. 14, 2006, and which are incorporated herein by reference.

FIELD OF THE INVENTION

The field of the present invention relates generally to specimen devices for collecting, storing, transporting and testing biological specimens. In particular, the present invention provides a tray for holding a plurality of biological specimen collection devices that facilitates the efficient organization, identification, sampling and testing of the biological samples.

BACKGROUND OF THE INVENTION

Collecting and testing biological specimens is conducted on daily basis in laboratories throughout the world. Examples of biological specimen testing includes DNA analysis, substance testing, urinalysis, serum/blood testing and genetic analysis. Prior to the introduction of automated mechanical technology, biological specimens were collected and tested manually. With the advent of automated mechanical technology, however, testing of biological samples has become more rapid and reliable.

One example of this automated technology involves the use of micro well plates or micro titer plates. The typical micro well plate is configured to have eight rows, each row having twelve wells (or 96 wells in the plate). Recently developed micro well plates have as many as 384 wells in the plate. Biological specimens first are collected in various ways including using an absorbent that retains the biological specimen in an efficient manner. The biological specimens are then transferred into the wells of a micro well plate or "plate" for subsequent analysis. One way to transfer the biological specimen to the plate is through a "punch" method. Typically, a device will punch an area of the absorbent containing the biological specimen into a particular well (A1, A2, A3, . . . A12)(FIG. 5) of a micro well plate. This process is repeated for each of the wells of the plate. Although the plates allow for the rapid analysis of a multitude of biological specimens, the process of transferring specimens to the wells of the plates is time consuming and prone to cross contamination and misidentification of the specimens inserted into the wells. For example, cross contamination may occur if the "punch" device used to remove a portion of the absorbent to be analyzed in the well is not cleaned prior to punching of a subsequent absorbent containing a different biological specimen. Also, with the use of large groups of specimens as may be found in the 96 well plates, there exists a higher chance of incorrectly labeling or identifying one of the 96 biological specimens placed into the wells of the plate. Finally, because of the sheer quantity of samples of biological specimens generated with the use of micro well plate assays, there is a vital need to organize, store and transport biological specimens contained on the absorbents of a specimen collector.

SUMMARY OF THE INVENTION

The present invention facilitates the collection, storage, identification, sampling and testing of biological specimens contained on an absorbent. The specimen collector with absorbent is placed on the designated location on the specimen tray. The specimen tray organizes the specimen collectors in a side by side fashion so that an automated process of testing the biological specimens may proceed in a rapid, convenient and accurate way. Also, the present invention provides several ways in which cross contamination of biological specimens may be prevented both in storing the devices and in sampling and testing the biological specimens. A further advantage of the present invention is that each device containing a biological sample is easily identified because of a unique code that is associated with the device. Yet another advantage of the present invention is the storage and transport of several devices in a convenient, organized and easily identifiable manner.

The above benefits and objectives are accomplished by a device which provides, in one embodiment, a specimen tray for retaining and holding in a spaced array a plurality of specimen collectors. An individual specimen collector comprises a handle having an absorbent extending from one end of the handle. The specimen tray is configured to align the absorbents of a plurality of specimen collectors adjacent a portion of a cleaning absorbent paper mounted on the specimen tray. In general the cleaning absorbent is mounted on the area of the specimen tray holding the absorbent ends of the specimen collectors. When a punch is used to take samples of the absorbent, the punch may be cleaned by punching the cleaning absorbent paper prior to moving on to the next absorbent to be punched.

In another embodiment, a different benefit is accomplished by use of unique identifying codes associated with an individual specimen collector. One example of such a unique identifying code is a barcode. In another embodiment, a plurality of specimen trays containing specimen collectors with absorbents are stacked on top of each other and stored in a second container. The configuration and separation of the specimen trays prevents cross contamination of biological specimens contained on the absorbents of the specimen collectors.

The foregoing and other objects are intended to be illustrative and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention.

DESCRIPTION OF THE DRAWINGS

Preferred embodiments of the invention, illustrative of the best modes in which the applicant has contemplated applying the principles, are set forth in the following description and are shown in the drawings and are particularly and distinctly pointed out and set forth in the appended claims.

Figure 3:
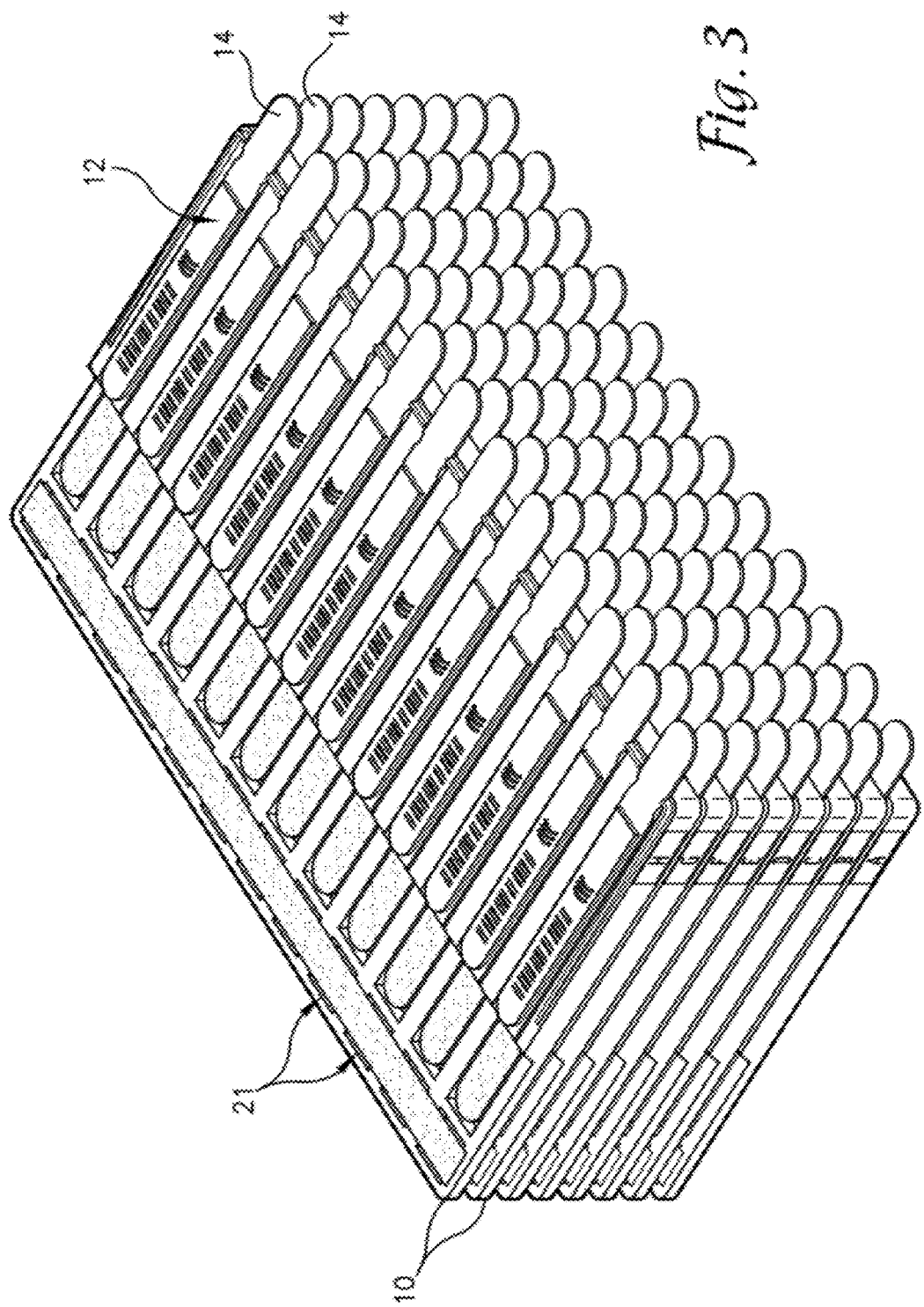
Figure 4:
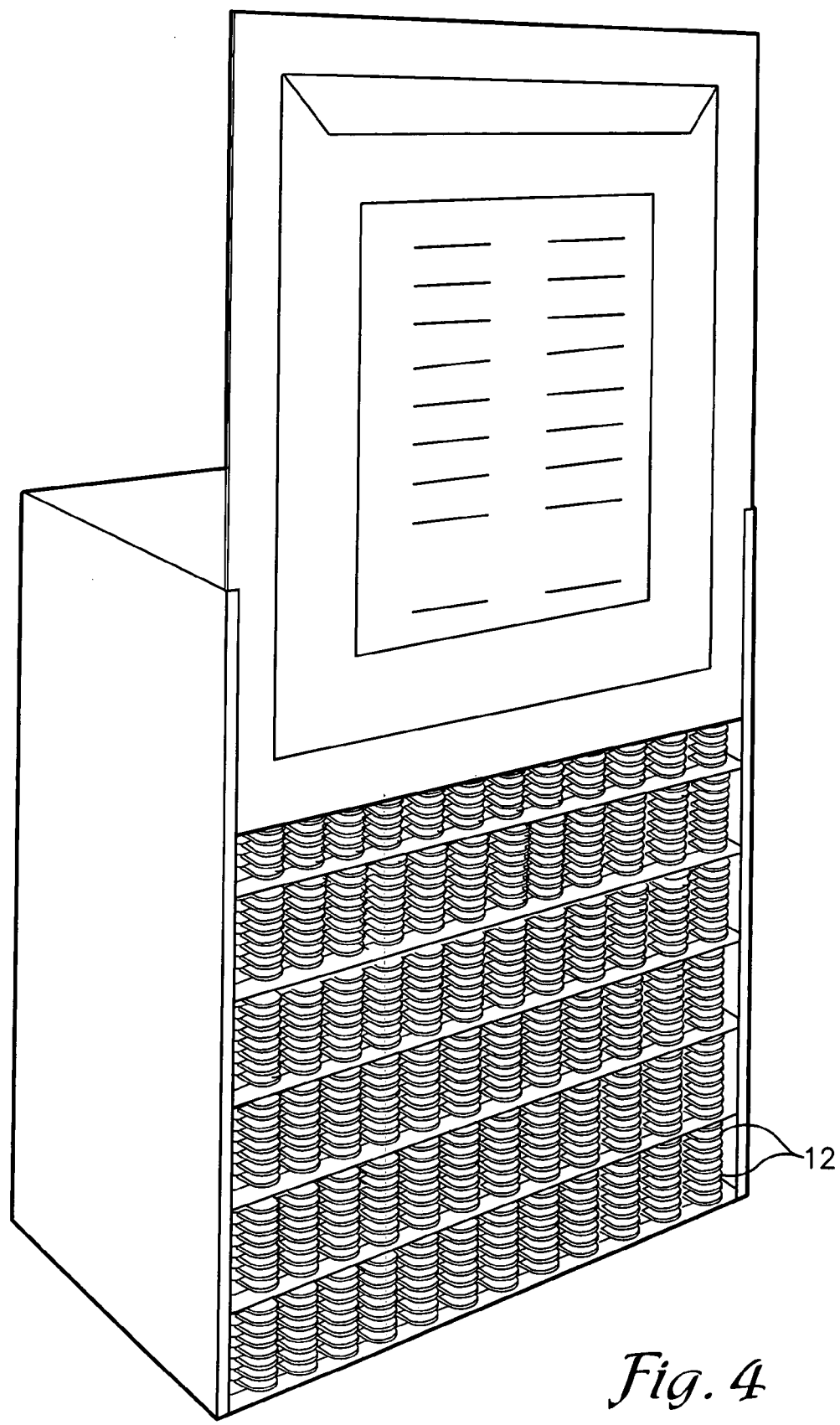
Figure 5:
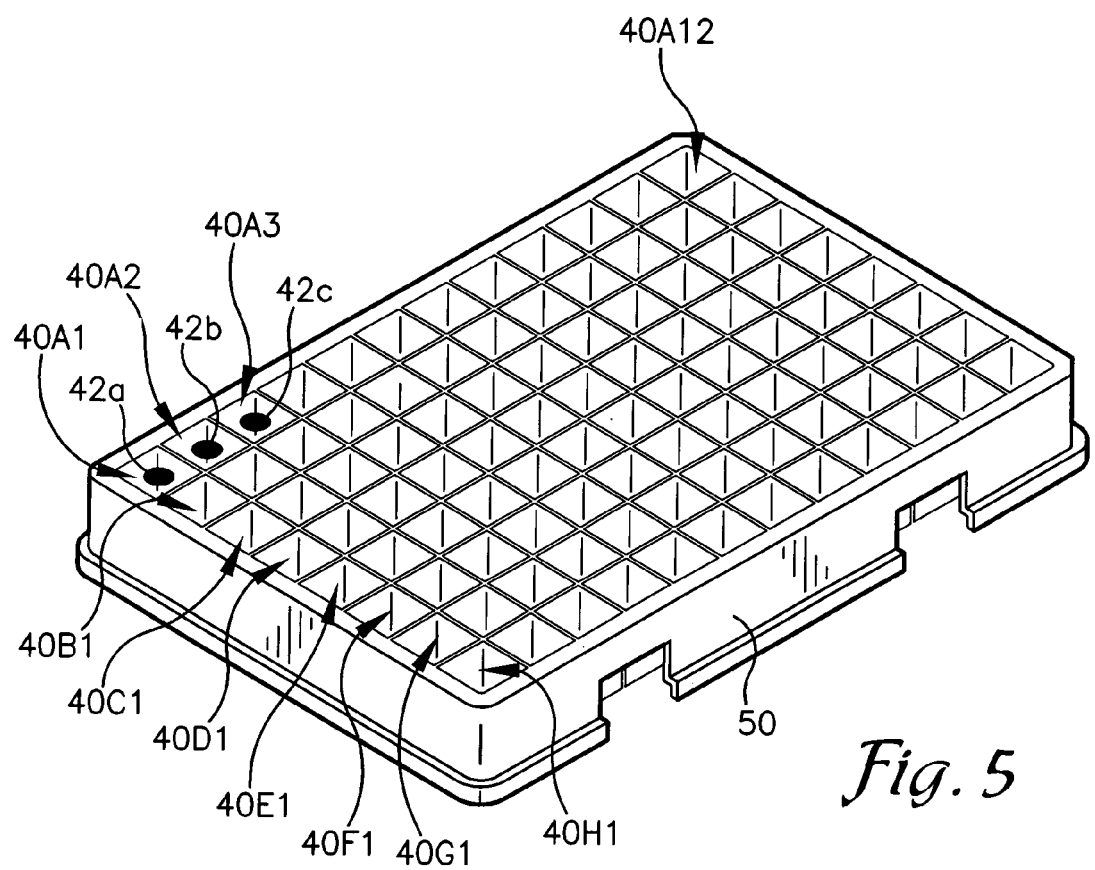

1, but having a reduced number of specimen collectors therein and suitable for use with a micro well plate by filling the columns of eight wells across the plate;

FIG. 3 is a front and left side perspective view of multiple specimen trays configured in a stacked arrangement to maintain the collector absorbents in spaced array to avoid contact and cross-contamination during storage of the collector absorbents;

FIG. 4 is a front and left side perspective view of a plurality of sets of multiple specimen trays in stacked arrangement that have been placed in a storage container for archival purposes and/or shipping;

FIG. 5 is a front and left side perspective view of a micro well plate of the type having 96 wells.

Figure 6:
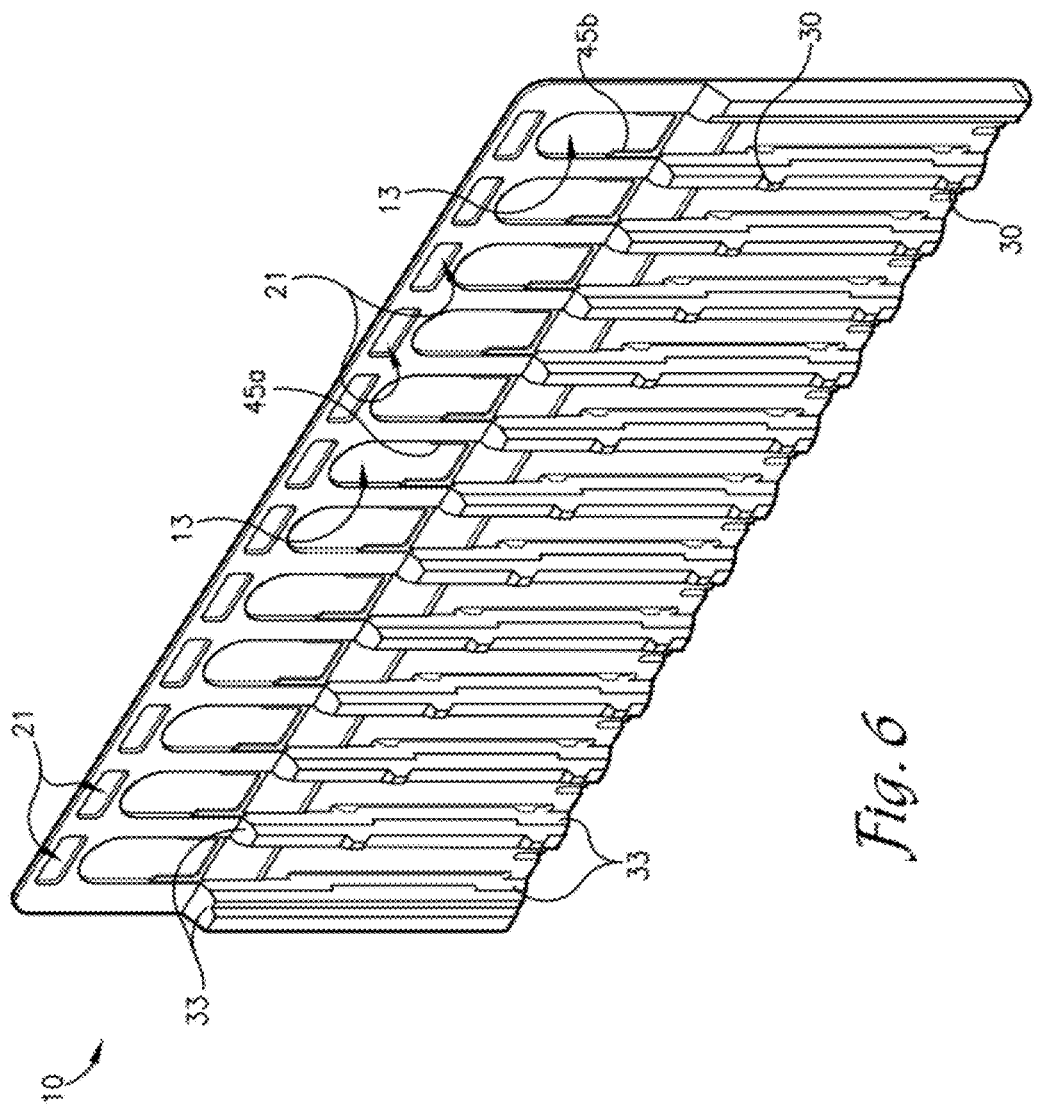

FIG. 6 is a top and right side perspective view of an embodiment showing shoulders 45a,b which support the absorbent as it is retained within the tray and showing the projecting feet 30 which allow a first tray to stackably register with indents 32 (FIG. 7) of a second tray for archival storage of the collectors; and FIG. 7 is a bottom and right side perspective view of the embodiment of FIG. 6 showing indents 32 which register with projecting feet 30 (FIG. 6) of an adjacent tray to allow stackable registration of trays for archival storage of the collectors fitted therein.

DETAILED DESCRIPTION

Figure 1:
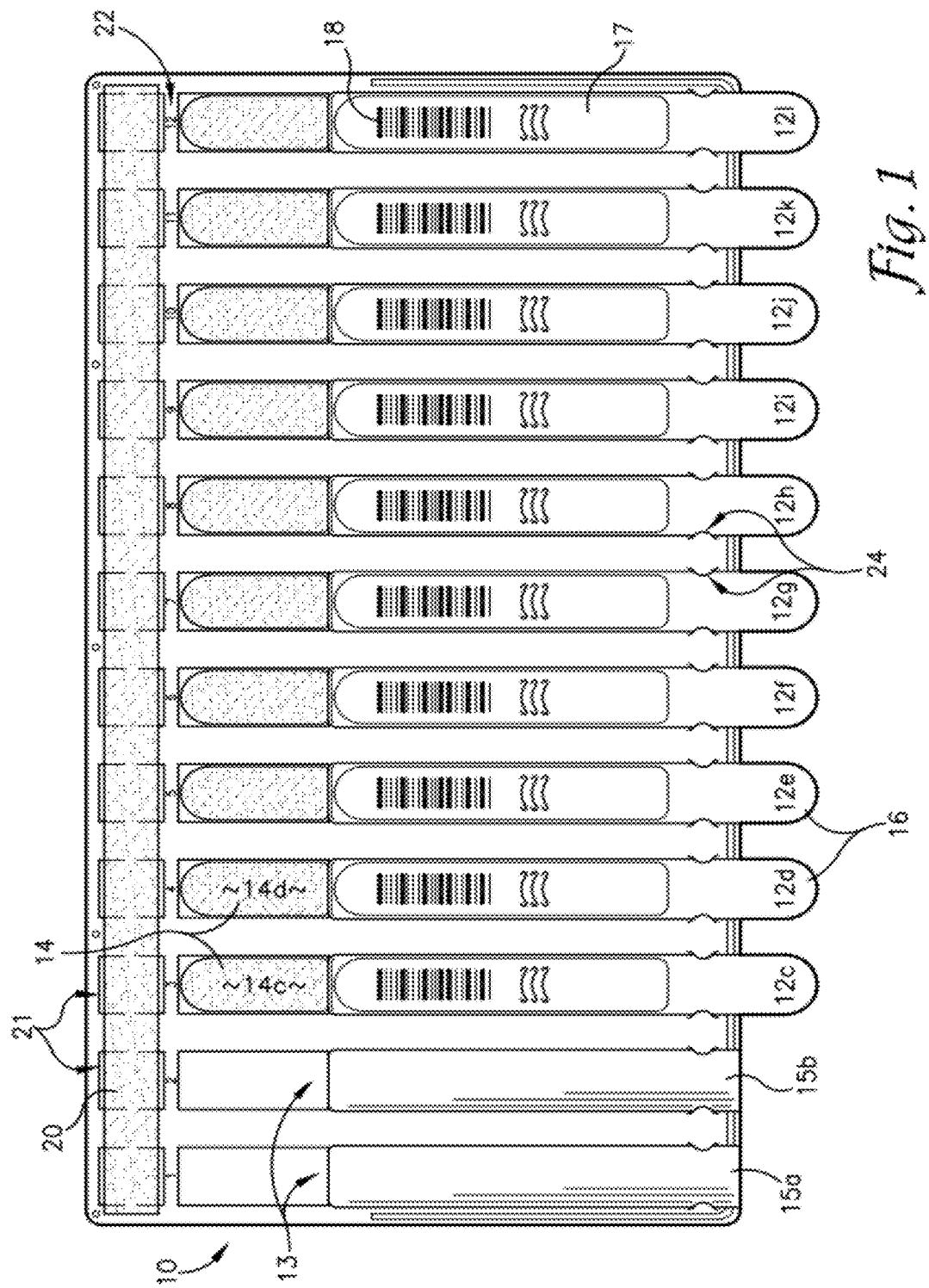
FIG. 1 is a top plan view of a first embodiment showing a plurality of specimen collectors with absorbents retained in side by side array in the tray holder slots numbered 1 thru 12 this first embodiment allowing the filling one row of a micro well tray and showing a cleaning absorbent paper strip across one edge of the specimen tray.

Referring to FIG. 1, an embodiment is shown which comprises a tray holder 10 for holding and storing biological specimen collectors 12c-12l within collector receivers 15c-12l and with collectors 12a and 12b not shown in collector receivers 15a and 15b. The specimen collectors comprise an absorbent 14 attached to a handle 16, and each is individually and uniquely identified by a bar code 18 on handle 16. The specimen collectors also may be provided with a slidable cover 17 mounted on handle 16 that allows the absorbent 14 to be covered for protection and uncovered for sample gathering or analysis after collection. Specimen collectors 12 are typically used in biological testing and forensic applications. A biological sample is placed onto absorbent 14 of specimen collector 12, and the specimen collector 12 generally is shipped to a testing laboratory for analysis of the biological specimen placed on absorbent 14. Such tests are conducted using various chemistry analyzers and other mechanical devices which operate in a highly efficient manner. One of the principal delays in accomplishing such specimen testing is the punching out of a sample portion from absorbent 14 and the placement of the punched out specimen portion into a well of a micro well plate as is shown in FIG. 5. Typically, such micro well plates come in various sizes, such as the configuration of 96 wells comprised of twelve wells across and eight such rows. A micro well plate having 96 wells is shown in FIG. 5.

Still referring to FIG. 1, device 10 allows for rapid arrangement of hundreds of specimen collectors 12 into a fixed side-by-side arrangement within tray 10. A void 13 is provided at a location in tray 10 that is immediately underneath the location of absorbent 14 when a collector 12 having absorbent 14 extending therefrom is inserted into one of collector receivers 15a-15l. As will be described hereinafter, void 13 allows a portion, or sample, punched out of absorbent 14 to fall into a well of a micro well plate 50 (FIG. 5). A cleaning absorbent paper 20 is provided closely positioned adjacent absorbent 14 and which can be used to clean a sample punch out device between the making of punches into absorbents 14. Through the use of specimen tray 10, a large volume of specimen collectors may be rapidly arranged into multiple trays 10 by a relatively unskilled individual and inserted into a sample punching machine. The sample punching machine can robotically extract one or more punches from each absorbent 14 of specimen collectors 12a-12l positioned within tray 10 and intermittently clean the punch head on cleaning absorbent paper 20. Cleaning is accomplished by punching cleaning absorbent paper 20 one or more times between the punching of the various absorbents 14. The portions punched from cleaning absorbent paper 20 are allowed to fall through cleaning void 21 (FIG. 6) and be discarded. This then allows a very high punch rate to be obtained and a very high rate of processing of hundreds of specimen collectors 12a-12l while maintaining accuracy of delivery of the punched out portion of absorbent 14 into a well of a micro well plate.

In operation, a laboratory worker receives a plurality of specimen collectors 12, each of which is separately enclosed in a shipping container. The technician removes each specimen collector 12 from its shipping container and places each collector 12 into a collection receiver 15a-15l as is indicated by the position number 22 (e.g., 1, 2, 3 . . . 12) shown in FIG. 1. Each specimen collector 12 is retained within a particular collection receiver 15a-15l of tray 10 by frictional fit against tabs 24. This allows the technician to press fit each specimen collector 12 into a collection receiver 15a-15l of tray 10 with the specimen collectors being retained in collection receiver 15 by frictional fit against tabs 24. Once the technician has arranged the proper number of specimen collectors 12a-12l into the collection receivers 15a-15l of tray 10 (in this case, 12 collectors can be fitted into tray 10 of FIG. 1) the tray is then inserted into the punch device.

During the punching operation, the punch device (not shown) positions tray 10 underneath the punch device so absorbent 14 of specimen collector 12a (not shown) which is residing in position 1 (22, FIG. 1) is positioned under the punch head. The punch device also aligns the appropriate well 40A1 (FIG. 5) of a micro well plate 50 (FIG. 5) beneath tray 10 (FIG. 1) so well 40A1 is directly beneath absorbent 14a of position 1 (22) of tray 10 to allow the punched out sample 42 (FIG. 5) from absorbent 14a to fall into the well 40A1 of micro well plate 50 therebelow. Once the absorbent sample has been punched from absorbent 14a, the punch then retracts and punches one or more times through cleaning absorbent paper 20, and specifically, in the portion of cleaning absorbent paper 20 located in front of position 2 of tray 10. A strip of cleaning absorbent paper 20 is located adjacent the top edge of the tray 10. This allows for cleaning of the punch head prior to extracting a new sample from the successive specimen collector 12b that resides within position 2 of tray 10. The previously described procedure is repeated such that a specimen is punched from each absorbent 14a-14l of the specimen collectors 12a-12l that have been inserted into positions 1-12 of tray 10.

Referring now to FIG. 5, once this procedure is repeated for the entire number of specimen collectors 12a-12l that have been inserted into tray 10 each of wells 40A1-40A12 of micro well plate 50 will have received one of punched samples 42a-42l (only punched samples 42a, 42b and 42c are shown in FIG. 5) thereby filling one row of micro well plate 50. At this point the punch device will automatically advance to the next tray 10 and re-align the wells of plate 50 to position a first absorbent 14a of second tray 10 over the first well 40B1 of the second row of wells in plate 50 to continue filling plate 50.

Figure 2:
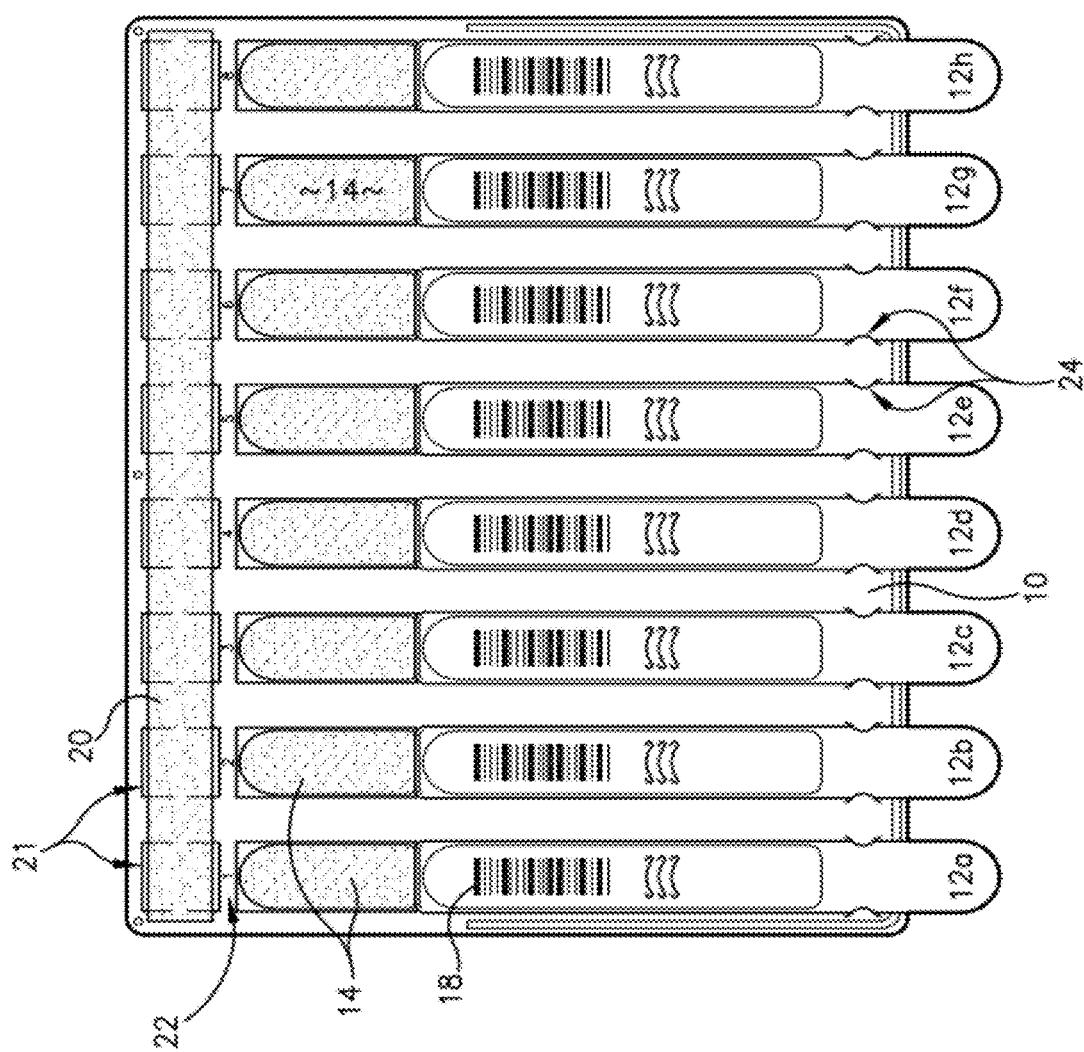
FIG. 2 is a top plan view of a second embodiment that shows a specimen collector tray that is similar to that of FIG.

Referring now to FIG. 2, an alternate embodiment is shown having eight specimen collectors 12a-12h arranged therein for use with a micro titer tray but with the punched samples from the absorbents being directed into the wells according to column order (See, FIG. 5, e.g. A1, B1, C1, . . . H1). This alternate embodiment can be operated upon in the manner previously described for the embodiment of FIG. 1.

Referring to FIG. 3, multiple specimen trays 10 are shown stacked for convenience of storage. The spacing of stacked trays 10 by feet 30 (FIG. 6) maintains a spaced array of collector absorbents 14 to provide separation between absorbents 14. This spaced array avoids cross contamination of the specimens on specimen collectors 12.

Referring to FIG. 4, the utility of specimen trays 10 may be seen in the ability to stack, store and ship large numbers of specimen collectors 12 and again without the potential for cross contamination of absorbents 14 as absorbents 14 are maintained and spaced apart arrangement.

Referring now to FIG. 5, a typical micro well plate 50 is shown of the 96 well configuration produced by twelve columns and eight rows of wells. Punched samples 42a, 42b and 42c are shown respectively within wells 40A1, 40A2 and 40A3, each sample residing within a well of the first row, or Row A, of the plate 50.

Referring now to FIGS. 6 and 7 a support structure for absorbent 14 of collector 12 is shown extending from the sidewalls adjacent void 13 of tray 10. Also the interrelationship between feet 30 (FIG. 6) and indents 32 (FIG. 7) will be described. Each void 13 of tray 10 may be provided with shoulders 45a, b which extend into void 13 from either side of tray 10. Shoulders 45a, b serve to support absorbent 14 as it resides within void 13. Shoulders 45a, b also provide a structure to resist the bending or drooping of absorbent 14 downwardly where it could contact other surfaces or other collectors and thereby become cross-contaminated by such extraneous contact with other surfaces. Shoulders 45a, b further provide support to absorbent 14 during the punching process by acting to resist the force of the punch device against absorbent 14 thereby retaining absorbent 14 in proper position and away from contact with extraneous surfaces. In FIGS. 6 and 7, feet 30 are shown (FIG. 6) and indents 32 are shown (FIG. 7). In the embodiment of FIGS. 6 and 7 feet 30 and indents 32 are opposite faces of the same structure and therefore present alignable, or registerable, structures which serve to allow the stacking of trays 10 into groups (FIG. 3) having the absorbents 14 spaced apart from one another to avoid cross-contamination. In this manner multiple trays 10 having multiple collectors 12 can be stacked together for archival storage of the collectors fitted therein. Also shown in FIGS. 6 and 7 are standoffs 33 which serve to space a first tray 10 from a second tray 10 stacked onto the first tray 10.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the device is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A specimen collector and specimen collector holder comprising:
    a specimen collector comprising:
        a handle having a first end and a second end, a collection absorbent extending from said first end of said handle for collection of a biological specimen thereon, and
        a cover slidably mounted on said handle for movement between a first absorbent covering position and a second absorbent exposing position,
    a specimen collector holder comprising:
        a tray having a top, a bottom surface, and four bounding edges,
        a plurality of spaced apart, elongate, holder positions within said tray, each position configured to receive and retain therein a specimen collector device,
        a plurality of voids in said tray said voids being adjacent to said holder positions for registration with the absorbent extending from said handle, and
        a cleaning strip affixed to said tray, the cleaning strip being positioned over a cleaning void in said tray, said cleaning strip being spaced from the absorbent to separate the cleaning strip from the absorbent and said cleaning strip being positioned between said collection absorbent and one of said bounding edges of said tray.

2. The device of claim 1 wherein each collection device is affixed with a unique identifying code.

3. The device of claim 1 wherein said specimen tray further comprises twelve receivers.

4. The device of claim 1 wherein said specimen tray further comprises eight receivers.

5. The device of claim 1 wherein said cleaning strip comprises a horizontal strip of cleaning paper adjacent the top edge of the specimen tray.

6. The device of claim 1 wherein the specimen tray further comprises opposed tabs extending into each of said receivers for frictional capture of said collection device therebetween.

7. The device of claim 1 further comprising a shoulder extending about at least a portion of each of said voids to support the absorbent.

* * * * *